United States Patent [19]

Bank

[11] Patent Number: 5,126,469
[45] Date of Patent: Jun. 30, 1992

[54] SUPPORTED CATALYSTS FOR ADDITION OF SILICON HYDRIDES TO α,β-UNSATURATED OLEFINIC NITRILES

[75] Inventor: Howard M. Bank, Freeland, Mich.

[73] Assignee: Dow Corning Corporation, Midland, Mich.

[21] Appl. No.: 719,451

[22] Filed: Jun. 24, 1991

[51] Int. Cl.$^5$ .............................. C07F 7/10
[52] U.S. Cl. .................................... 556/415
[58] Field of Search ......................... 556/415

[56] References Cited

U.S. PATENT DOCUMENTS 2,860,153 11/1958 Saam .................................. 556/415
2,906,764 9/1959 Jex et al. ............................ 556/415
2,971,970 2/1961 Bluestein ........................... 556/415
2,971,972 2/1961 Bluestein ........................... 556/415

OTHER PUBLICATIONS

Rajkumar et al., Organometallics 8, 550–552, 1989.
Svoboda et al., Collection Czechoslov. Chem. Commun. 38, 3834–3836, 1973.

*Primary Examiner*—Paul F. Shaver
*Attorney, Agent, or Firm*—William F. Boley

[57] ABSTRACT

The present invention is a process for the preparation of hydrolyzable β-cyanoalkylsilanes. More particularly, this invention relates to the catalytic addition of hydrolyzable silicon hydrides to α,β-unsaturated olefinic nitriles to form β-cyanoalkylsilanes. The instant process employs a catalyst comprising a diamine and supported copper or a supported copper compound.

21 Claims, No Drawings

SUPPORTED CATALYSTS FOR ADDITION OF SILICON HYDRIDES TO α,β-UNSATURATED OLEFINIC NITRILES

BACKGROUND OF INVENTION

The present invention is a process for the preparation of hydrolyzable β-cyanoalkylsilanes. More particularly, this invention relates to the catalytic addition of silicon hydrides to α,β-unsaturated olefinic nitriles to form β-cyanoalkylsilanes. The instant process employs a catalyst mixture comprising a diamine and supported copper or a supported copper compound.

Hydrolyzable β-cyanoalkylsilanes are useful for the production of polyorganosiloxanes containing the β-cyanoalkyl substituent. The silicon-bonded β-cyanoalkyl radical is extremely resistant to hydrolysis and cleavage under hot, humid conditions. Therefore, the β-cyanoalkylsilanes find particular use in the preparation of polyorganosiloxanes which must be subjected to hot humid conditions. The presence of the silicon-bonded β-cyanoalkyl radical substituted on polyorganosiloxanes also tends to stabilize the polyorganosiloxanes against swelling induced by liquid hydrocarbons.

Bluestein, U.S. Pat. No. 2,971,970, issued Feb. 14, 1961, describes a method for forming cyanoalkylsilanes. The method comprises reacting a hydrolyzable silicon hydride with an α,β-unsaturated olefinic nitrile in the presence of a diamine and a cuprous compound selected from the class consisting of cuprous oxide and cuprous halides.

Rajkumar et al., Organometallics 8. 550-552. 1989, describes a two-component catalyst, consisting of cuprous oxide and tetramethylethylenediamine, that promotes β-hydrosilylation of acrylonitrile.

Svoboda et al., Collection Czechoslov. Chem. Commun. 38, 3834-3836, 1973, describes binary systems of a copper compound (Cu(I) oxide, Cu(I) chloride, or Cu(II) acetylacetonate) and an isocyanide (tert-butyl or cyclohexyl isocyanide) as effective catalysts for hydrosilylation of acrylonitrile by trichlorosilane and methyldichlorosilane.

The present process employs a catalyst, comprising a diamine and supported copper or a supported compound of copper, which promotes the β-hydrosilylation of unsaturated olefinic nitriles by silicon hydrides. The use of supported copper or a supported copper compound as a component of the catalyst permits retention of the supported copper component in continuous processes and easy recovery and reuse of the supported copper component in batch type processes.

SUMMARY OF INVENTION

The present invention is a process for the preparation of hydrolyzable β-cyanoalkylsilanes. More particularly, this invention relates to the catalytic addition of hydrolyzable silicon hydrides to α,β-unsaturated olefinic nitriles to form β-cyanoalkylsilanes. The instant process employs a catalyst comprising a diamine and supported copper or a supported copper compound.

DESCRIPTION OF INVENTION

The present invention is a process for preparation of β-cyanoalkylsilanes of formula:

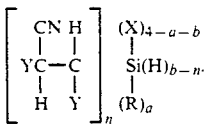 (1)

The process comprises contacting a silicon hydride of formula $$R_aH_bSiX_{4-a-b}, \quad (2)$$

with an unsaturated olefinic nitrile of formula

 (3)

in the presence of a catalyst comprising a diamine of formula $$R^1R^2NR^3NR^2_2, \quad (4)$$

and supported copper and the supported copper is selected from a group consisting of copper and copper compounds retained on a solid support; where each R is independently selected from a group consisting of monovalent hydrocarbon radicals, substituted monovalent hydrocarbon radicals, alkoxy radicals, and aryloxy radicals; $R^1$ is a lower alkyl radical; $R^2$ is selected from a group consisting of hydrogen, lower alkyl radicals, aminoalkyl radicals, alkylaminoalkyl radicals, dialkylaminoalkyl radicals, and mixtures thereof; $R^3$ is an unsubstituted bivalent radical selected from a group consisting of alkylenes and alkenylenes of less than nine carbon atoms; X is a halide atom; each Y is independently selected from a group consisting of hydrogen and lower alkyl radicals of 1 to 8 carbon atoms; n=1, 2, or 3; a=0, 1, or 2; b=1, 2, or 3; and a+b=1, 2, or 3.

In carrying out the reaction of the present invention, the unsaturated olefinic nitrile, the silicon hydride and the supported copper or supported copper compound are contacted in a suitable reaction vessel. The type of reaction vessel is not critical. The reaction can be run as a batch or as a continuous process. The reactor can be, for example, a packed-bed, a stirred-bed, a vibrating-bed, or a fluidized-bed type reactor. Preferred is a continuous process where the supported copper or supported copper compound is present as a packed bed.

The time required for effecting the reaction varies depending on the particular reactants, the particular catalyst mixture employed and the temperature of the reaction. In general reaction times of 0.5 to 18 hours have been found useful. A preferred reaction time is about 0.2 to three hours.

The temperature for conducting the process may be within a range of about 50° C. to about 200° C. It is preferred that the temperature be within a range of about 70° C. to about 150° C. Generally, higher temperatures allow the use of a catalyst with a lower copper concentration, but at temperatures above about 150° C. undesired by-products may be produced.

The silicon hydride, Formula 2, employed in the present invention can contain from one to three silicon-bonded hydrogens and from one to three silicon-bonded halide atoms. The halide atom, X, can be selected from the group consisting of fluoride, chloride, bromide and iodide. The preferred halide is chloride.

The silicon hydride can contain up to two radicals, R, selected from a group comprising monovalent hydrocarbon radicals, alkoxy radicals, aryloxy, and substituted monovalent hydrocarbon radicals, where the substituent is inert with respect to the addition reaction. The radical, R, can be, for example, alkyl radicals e.g., methyl, ethyl, butyl, octyl, and octadecyl. The preferred alkyl is when R is a lower alkyl radical containing from 1 to 8 carbon atoms. The radical, R, can be, for example, aryl radicals. e.g. phenyl, naphthyl, diphenyl, tolyl, xylyl, and ethylphenyl. The preferred aryl radical is phenyl. The radical, R, can be, for example: aralkyl. e.g., benzyl and phenylethyl; haloaryl, e.g., chlorophenyl, dibromophenyl and chloronaphthyl; cyanoalkyl, e.g., $\beta$-cyanoethyl, $\beta$-cyanopropyl, and $\beta$-cyanobutyl; cycloalkyl, e.g., cyclohexyl and cycloheptyl; alkenyl. e.g., vinyl and allyl; substituted alkyl, e.g. 3,3,3-trifluoropropyl; alkoxy, e.g. methoxy, ethoxy, and propoxy; and aryloxy, e.g. phenoxy. The most preferred radical, R, is methyl. The preferred silicon hydride is selected from a group consisting of methyldichlorosilane and trichlorosilane.

The silicon hydride is contacted with an $\alpha,\beta$-unsaturated olefinic nitrile, described by Formula 3 and containing substituents Y, where each Y is independently selected from a group consisting of hydrogen and lower alkyl radicals. By "lower alkyl radicals" is meant, alkyl radicals having from 1 to 8 carbon atoms. The unsaturated olefinic nitrile can be, for example, acrylonitrile, methacrylonitrile, crotononitrile, ethylacrylonitrile, 1-cyanobutene-1, or 2-cyanooctene-1.

The catalyst consists of a diamine and supported copper or a supported copper compound. The combined presence of the diamine and supported copper or supported copper compound is necessary to form an effective catalyst. The catalyst can be preformed as a mixture and added to the instant process or the diamine and supported copper or supported copper compound can be added separately to the process.

By "supported" is meant elemental copper or a copper compound retained on a solid support. The supported copper compound can be an inorganic or organic copper compound retained on a solid support. The solid support can contain copper or copper in combination with one or more copper compounds. The solid support can contain one or more copper compounds.

The inorganic copper compound can be selected from a group consisting of, for example, copper halide, copper oxide; copper sulfate, copper sulfide, and copper cyanide compounds; Cu(I) thiocyanide; and copper chromium compounds. The copper halide can be, for example, Cu(I) chloride, Cu(I) bromide, Cu(I) iodide, Cu(I) fluoride. Cu(II) chloride, Cu(II) bromide, Cu(II) iodide, and Cu(II) fluoride. The copper oxide can be, for example, Cu(I) oxide or Cu(II) oxide. The copper sulfate can be, for example, Cu(I) sulfate and Cu(II) sulfate. The copper sulfide can be, for example, Cu(I) sulfide and Cu(II) sulfide. The copper cyanide compound can be, for example, Cu(I) cyanide and Cu(II) cyanide. The copper chromium compounds can be, for example: Cu(II) chromate, e.g., $CuCrO_4.2CuO.2H_2O$; Cu(II) dichromate, e.g., $CuCr_2O_7.2H_2O$; and Cu(I) chromite. e.g., $Cu_2Cr_2O_4(2CuOCr_2O_3)$.

A preferred inorganic copper compound can be selected from a group consisting of Cu(I) oxide, Cu(II) oxide, Cu(I) chloride and Cu(II) chloride. The most preferred inorganic copper compound is Cu(II) oxide.

The supported copper compound can be an organic copper compound. Preferred is when the organic copper compound is a di-coordinate organic copper compound. By "di-coordinate organic copper compound" is meant compounds of general formula $Cu(R^4)_2$: where $R^4$ is a radical of formula: $-OR^5$, $-OOCR^5$,

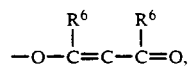

and aryl; where $R^5$ is selected from a group consisting of alkyl. alkenyl, and aryl radicals of less than 25 carbon atoms and $R^6$ is selected from a group consisting of hydrogen and hydrocarbon radicals of less than seven carbon atoms.

The di-coordinate organic copper compound can be, for example, Cu(II) methoxide, Cu(II) ethoxide, Cu(II) allyloxide, Cu(II) acetate. Cu(II) stearate, Cu(II) tetramethylheptanedionate, Cu(II) acetylacetonate, Cu(II) naphthanate, and Cu(II) phenylate.

The copper or copper compound is retained on a solid support. The method of retention of the copper or copper compound on the solid support is not critical to the present invention. It is preferred that copper or the copper compound not be released from the solid support during conduct of the process. The copper or copper compound may be retained on or within the solid support by standard means, for example, adsorption, ionic bonding, covalent bonding, or physical entrapment.

The solid support material can be any material capable of retaining the copper or copper compound under process conditions. The solid support material can be, for example, silicon metalloid, silica, silica gel, alumina, carbon, graphite, ceramic, or zeolite. The silica can be, for example, a fumed or precipitated silica. Preferred is when the solid support material is metallurgical grade silicon or silica gel.

The solid support material can be in the form of, for example, flakes, chips, particles, powders, spheres, or tablets. Preferred is when the solid support material is less than about one centimeter in diameter. More preferred is when the solid support material is less than about 0.5 centimeter in diameter. The lower size limit for the solid support material is determined by the practicalities of retaining, recovering, and handling of the material.

Copper supported on metallurgical grade silicon or silica gel is a preferred supported copper component for the catalyst. Copper halides and copper oxides supported on metallurgical grade silicon or on silica are preferred supported copper compounds. The most preferred supported copper compounds are Cu(I) chloride and Cu(II) oxide.

A useful concentration of copper retained on the solid support, either in the form of elemental copper or copper compound, is where the weight of copper is within a range of about 0.5 to 30 weight percent of the weight of the solid support. Lower concentrations of copper may be used, but the product production rate may be reduced. Preferred is when the concentration of copper retained on the solid support, either in the form of elemental copper or copper compound, is within a range of 0.5 to 5 weight percent of the weight of the solid support.

The diamine is as described by Formula 4, where $R^1$ is a lower alkyl radical of 1 to 8 carbon atoms; $R^2$ is selected from a group consisting of hydrogen, lower alkyl radicals of 1 to 8 carbon atoms, aminoalkyl radicals, alkylaminoalkyl radicals, dialkylaminoalkyl radicals, and mixtures thereof; and $R^3$ is an unsubstituted bivalent radical selected from the group consisting of alkylenes and alkenylenes of less than 9 carbon atoms. The diamine can be, for example, N,N,N', N'-tetramethylethylenediamine, N,N,N',N'-tetraethylethylenediamine, N,N,N'-trimethylethylenediamine, N,N-dimethyl-N'.N'-diethylethylenediamine, N,N-dimethylethylenediamine, N-methyl-N,N',N'-triethylethylenediamine, N,N,N',N'',N''-pentamethyldiethylenetriamine, N,N,N'-trimethyl-N-'-ethylethylenediamine, N,N,N',N'-tetramethylmethylenediamine, N,N'N'',N''-tetramethyldiethylenetriamine, N,N,N',N'-tetramethyldiethylenetriamine, and N-methylhexamethylenediamine. The preferred diamine is N,N,N',N'-tetramethylethylenediamine.

Although not necessary, it is preferred that the contents of the reactor be mixed during conduct of the instant method, particularly when the process is run as a batch process. Mixing can be accomplished by standard means, for example, mechanical stirring, refluxing, sonification, or mixing during addition to the reactor.

The catalyst can comprise on a molar ratio basis about 0.1 to 20 moles of diamine per mole of copper, the copper present either as supported copper or supported copper compound. In general, as the temperature of the process is increased a lower ratio of diamine to copper is required. A preferred mole ratio of diamine to copper is about 0.2 to 2.0.

The amount of catalyst employed in relation to the amount of unsaturated olefinic nitrile may be varied within extremely wide limits. However, it is preferred to run the process under conditions where the mole ratio of copper to unsaturated olefinic nitrile is in a range of about 0.01 to 1.0. A more preferred ratio of copper to unsaturated olefinic nitrile is in a range of about 0.08 to 0.5.

When the instant process is run as a continuous process, the supported copper or supported copper compound can be separately contacted with a diamine at molar ratios as described for the batch process. It is believed that the diamine complexes with the copper and is partially retained by the supported copper or supported copper compound to maintain an active catalyst mixture. However, during the continuous process it may be necessary to reactivate the catalyst by addition of diamine to the process. The diamine required to reactivate the catalyst may be added separately to the supported copper or supported copper compound or may be added as a mixture with feed materials to the process.

The ratio of the silicon hydride to the unsaturated olefinic nitrile may be varied within wide limits. However, since the preferred process involves adding one mole of the silicon hydride to one mole of the unsaturated olefinic nitrile, in a preferred embodiment of the invention about equimolar amounts of these reactants are employed. More preferred is where the silicon hydride is present in about a ten percent molar excess in relation to the unsaturated olefinic nitrile. The use of other molar excesses of either of the two reactants is not precluded, however no particular advantage is derived.

The described method is applicable to the production of β-cyanoalkylsilanes, as described by Formula 1. The preferred β-cyanoalkylsilanes, within the scope of Formula 1, are β-cyanoethylmethyldichlorosilane and β-cyanoethyltrichlorosilane. However, the instant process is also applicable to the preparation of hydrolyzable silanes containing more than one silicon-bonded β-cyanoalkyl radical, for example, bis-(β-cyanoethyl)-dichlorosilane and tris-(β-cyanoethyl)chlorosilane, by the addition of one mole of silicon bi- or tri-hydride to more than one mole of unsaturated olefinic nitrile. Other examples of β-cyanoalkylsilanes that can be made by the method of this invention, within the scope of Formula 1, are: β-cyanoethyltrichlorosilane β-cyanoethylmethyldichlorosilane, β-cyanoethylethyldichlorosilane, β-cyanopropyltrichlorosilane, β-cyanobutyloctyldichlorosilane, β-cyanoethylphenyldichlorosilane, β-cyanoethyldiphenylchlorosilane, β-cyanoethylmethylphenylchlorosilane, β-cyanoethylcyclohexyliodochlorosilane, α-ethyl-β-cyanoethylmethyldichlorosilane, β-cyanoethylvinyldichlorosilane, and β-cyanoethylchlorosilane.

In order that those skilled in the art may better understand how the present invention may be practiced, the following examples are given. These examples are given for illustration and are not meant to be limiting on the instant claims.

Example 1. A comparative study of the ability of catalysts mixtures comprising tetramethylethylenediamine (TMEDA) and supported copper to effect the addition of methyldichlorosilane to acrylonitrile to form β-cyanoethylmethyldichlorosilane was evaluated. The process was carried out in sealed tubes at a temperature of 100° C. The supported copper materials tested are presented in Table 1. The supported copper on silicon test materials were prepared by precipitating copper onto ground silicon. The CuO on silica and CuO on Al$_2$O$_3$ test materials were obtained from United Catalyst (Louisville, Ky.) as pellets impregnated with CuO. The pellets were crushed into a powder prior to use. The supported copper materials were dried at 120° C. before use.

In proceeding order, acrylonitrile, methyldichlorosilane, and TMEDA were added to tubes containing the supported copper material. The molar ratio of copper to acrylonitrile (Cu/AN) and the molar ratio of TMEDA to copper (TMEDA/Cu) are presented in Table 1. At times presented in Table 1, the contents of individual tubes were analyzed by gas liquid chromatography using a flame ionization detector (GLC-FID).

The results are expressed as the normalized area percent of β-cyanoethylmethyldichlorosilane present (% β-CEMDS), uncorrected for response factors. Normalization of the results were effected by subtracting the area under the GLC readout graph attributed to TMEDA and high boiling materials from the total area under the GLC readout graph and expressing β-cyanoethylmethyldichlorosilane present as an area percent of the remaining area under the readout graph.

TABLE 1

| Effect of Supported Copper on Catalyst Activity in Effecting Reaction of Methyldichlorosilane with Acrylonitrile. | | | | |
|---|---|---|---|---|
| | | | % β-CEMDS | |
| Copper/Support | Cu/AN | TMEDA/Cu | 3 h | 7.5 h |
| 0.5% Cu on Silicon | 0.004 | 125.00 | 5.2 | 15.4 |
| 2.0% Cu on Silicon | 0.016 | 31.24 | 30.8 | 67.9 |
| 25% CuO on Silica | 0.110 | 4.72 | 93.3 | 90.6 |
| 11% CuO on Al$_2$O$_3$ | 0.090 | 5.88 | 90.1 | 93.1 |
| Cu metal (Powder) | 0.340 | 1.47 | 18.5 | 42.4 |

Example 2. A comparative study of the ability of catalyst mixtures comprising tetramethylethylenediamine (TMEDA) and supported copper to effect the addition of trichlorosilane to acrylonitrile to form β-cyanoethyltrichlorosilane was evaluated. The process was carried out as described in Example 1. The supported copper materials tested, as presented in Table 2, are described in Example 1. The molar ratio of copper to acrylonitrile (Cu/AN) and the molar ratio of TMEDA to copper (TMEDA/Cu) are presented in Table 2. After one hour of heating, the contents of individual tubes were analyzed by GLC utilizing a thermal conductivity detector. The results are expressed as the normalized area percent of β-cyanoethyltrichlorosilane (% CETS), uncorrected for response factors. The results were normalized in a manner similar to that used to normalize the results for Example 1.

TABLE 2

Effect of Supported Copper on Catalyst Activity in Effecting Reaction of Trichlorosilane with Acrylonitrile.

| Copper/Support | Cu/AN | TMEDA/Cu | % β-CETS |
|---|---|---|---|
| 2.0% Cu on Silicon | 0.01 | 3.02 | 47.7 |
| 25% CuO on Silica | 0.11 | 1.47 | 32.6 |
| 11% CuO on Al$_2$O$_3$ | 0.09 | 1.47 | 0.8 |

What is claimed is:

1. A process for preparation of β-cyanoalkylsilanes of formula

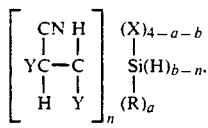

the process comprising:
contacting a silicon hydride of formula $$R_aH_bSiX_{4-a-b}$$

with an unsaturated olefinic nitrile of formula

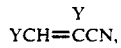

in the presence of a catalyst comprising a diamine of formula $$R^1R^2NR^3NR^2_2$$

and supported copper, and the supported copper is selected from a group consisting of copper and copper compounds retained on a solid support; at a temperature within a range of about 50° C. to 200° C.;

where each R is independently selected from a group consisting of monovalent hydrocarbon radicals, substituted monovalent hydrocarbon radicals, alkoxy radicals, and aryloxy radicals, R$^1$ is a lower alkyl radical, R$^2$ is selected from a group consisting of hydrogen, lower alkyl radicals aminoalkyl radicals, alkylaminoalkyl radicals, dialkylaminoalkyl radicals, and mixtures thereof; R$^3$ is an unsubstituted bivalent radical selected from a group consisting of alkylenes and alkenylenes of less than nine carbon atoms; X is a halide; each Y is independently selected from a group consisting of hydrogen and lower alkyl radicals of 1 to 8 carbon atoms; n=1, 2, or 3; a=0, 1, or 2; b=1, 2, or 3; and a+b=1, 2, or 3.

2. A process according to claim 1, where the process is a continuous process and the supported copper is present as a packed bed.

3. A process according to claim 2, where the temperature is within a range of about 70° C. to 150° C.

4. A process according to claim 2, where the silicon halide is selected from a group consisting of methyldichlorosilane and trichlorosilane.

5. A process according to claim 2, where the unsaturated olefinic nitrile is selected from a group consisting of acrylonitrile, methacrylonitrile, crotononitrile, ethylacrylonitrile, 1 cyanobutene-1, and 2-cyanooctene-1.

6. A process according to claim 5, where the unsaturated olefinic nitrile is acrylonitrile.

7. A process according to claim 2, where the supported copper is a copper compound retained on a solid support.

8. A process according to claim 7, where the supported copper is an inorganic copper compound retained on a solid support.

9. A process according to claim 8, where the copper compound retained on a solid support is an inorganic copper compound selected from the group consisting of Cu(I) oxide, Cu(II) oxide, Cu(I) chloride and Cu(II) chloride.

10. A process according to claim 9, where the copper compound retained on a solid support is Cu(II) oxide.

11. A process according to claim 2, where the supported copper is copper retained on a solid support.

12. A process according to claim 2, where the solid support is selected from a group consisting of silicon and silica gel.

13. A process according to claim 2, where the supported copper is copper retained on a solid support selected from a group consisting of silicon and silica gel.

14. A process according to claim 2, where the supported copper is Cu(II) oxide retained on silica gel.

15. A process according to claim 2, where the supported copper is an organic copper compound retained on a solid support.

16. A process according to claim 15, where the organic copper compound is a di-coordinate copper compound selected from a group consisting of Cu(II) methoxide, Cu(II) ethoxide, Cu(II) allyloxide, Cu(II) acetate, Cu(II) stearate, Cu(II) tetramethylheptanedionate, Cu(II) acetylacetonate, Cu(II) naphthanate, and Cu(II) phenylate.

17. A process according to claim 2, where the β-cyanoalkylsilane is β-cyanoethylmethyldichlorosilane.

18. A process according to claim 2, where the β-cyanoalkylsilane is β-cyanoethyltrichlorosilane.

19. A process according to claim 2, where the catalyst comprises about 0.2 to 2.0 moles of the diamine per mole of copper.

20. A process according to claim 2, where mole ratio of supported copper to unsaturated olefinic nitrile is within a range of about 0.08 to 0.5.

21. A process according to claim 2, where the halide is chloride.

* * * * *